United States Patent
Ellis et al.

(10) Patent No.: US 7,723,491 B1
(45) Date of Patent: *May 25, 2010

(54) METHODS OF ISOLATING SPECIFIC COMPOUNDS FROM SUPRAMAMMARY LYMPH NODE TISSUE

(75) Inventors: Steven E. Ellis, Central, SC (US); Thomas R. Scott, Central, SC (US)

(73) Assignee: Clemson University

( * ) Notice: Subject to any disclaimer, the term of this patent is extended or adjusted under 35 U.S.C. 154(b) by 92 days.

This patent is subject to a terminal disclaimer.

(21) Appl. No.: 11/753,894

(22) Filed: May 25, 2007

(51) Int. Cl.
C07K 14/00 (2006.01)
C07K 17/00 (2006.01)
A61K 35/12 (2006.01)
A61K 35/26 (2006.01)
C08H 1/02 (2006.01)

(52) U.S. Cl. .............. 530/412; 424/572; 424/578; 530/350; 530/351; 530/413; 530/422

(58) Field of Classification Search ............ None
See application file for complete search history.

(56) References Cited

U.S. PATENT DOCUMENTS

| | | | |
|---|---|---|---|
| 4,374,828 A | 2/1983 | Folkers et al. | |
| 4,520,107 A | 5/1985 | Healy et al. | |
| 4,785,079 A * | 11/1988 | Gospodarowicz et al. | ... 530/399 |
| 5,053,234 A | 10/1991 | Anderson et al. | |
| 5,070,076 A | 12/1991 | Morozov et al. | |
| 5,543,058 A | 8/1996 | Miller | |
| 6,770,199 B1 | 8/2004 | Taylor et al. | |
| 6,800,739 B2 | 10/2004 | Davis et al. | |
| 6,900,056 B2 | 5/2005 | Lee et al. | |

FOREIGN PATENT DOCUMENTS

WO WO 0004911 2/2000

OTHER PUBLICATIONS

Alluwaimi et al., the cytokines of bovine mammary gland: prospects for diagnosis and therapy, 2004, Research in Veterinary Science, vol. 77, pp. 211-222.*
Waller et al., Cytokines in mammary lymph and milk during endotoxin-induced bovine mastitis, 2003, Research in Veterinary Science, vol. 74, pp. 31-36.*
Weber et al., Contribution of Insulin-like growth factor (IGF)-I and IGF-binding protein-3 to mitogenic activity in bovine mammary extracts and serum, 1999, Journal of Endocrinology, vol. 161, pp. 365-373.*

* cited by examiner

*Primary Examiner*—Robert Landsman
*Assistant Examiner*—Ian Dang
(74) *Attorney, Agent, or Firm*—Dority & Manning, P.A.

(57) ABSTRACT

Methods of forming proteinaceous products such as cell culture supplement capable of supporting the growth and culturing of cells, tissue, and organs, are generally disclosed. One method generally provides for the collection of the internal tissue of an animal, such as a bovine, and the processing of the internal tissue to degrade and/or lyse the tissue components. A cell culture supplement or other proteinaceous product can be prepared from the processed tissue. A proteinaceous product can include, for example, a complete protein profile of the tissue or only certain biological factors extracted from the tissue. Collected internal tissue can be lymphatic tissue such as the supramammary glands of a dairy or beef cow or the thymus gland of a veal calf.

22 Claims, 6 Drawing Sheets

METHODS OF ISOLATING SPECIFIC COMPOUNDS FROM SUPRAMAMMARY LYMPH NODE TISSUE

BACKGROUND

Culture serum, such as Fetal Bovine Serum ("FBS"), is a culture medium supplement commonly used for in vitro culturing of cells and tissue. For instance, FBS can be utilized to promote cell growth and facilitate protein production. Culture serum is generally derived from blood via removal of the clotting factors and blood cells, typically by centrifugation after the red blood cells have been allowed to clot.

Unfortunately, culture serum, especially FBS, is expensive. Furthermore, serum has a limited range of components to support cell growth, with albumin and gamma globulins being the primary proteinaceous components. As such, additional materials have been used in combination with or as replacement for serum to help control and promote cell growth and lower costs. For example, natural animal-derived biological factors, such as purified primatone and albumin, have been used as serum replacements as well as serum additives in cell culturing. However, the quality of known animal-derived materials can vary from batch to batch, which can lead to inconsistent or even unpredictable cell growth in the culture. Moreover, these materials can also be extremely expensive to produce.

A need currently exists for culturing supplements that can be inexpensively provided in commercially useful amounts. Also, a need exists for culture supplements that can provide consistent and predictable cell growth in the utilizing cultures. Also, a need exists for economical methods for providing specifically designed and tailored preparations, and specifically preparations including a well defined protein profile and/or a minimum number of purified biological factors such as proteins, lipids, fatty acids, and the like.

SUMMARY

In one embodiment, disclosed is a method of isolating one or more specific growth factors from internal tissue of an animal. For instance, the method can include collecting supramammary lymph node tissue from an animal carcass (e.g., bovine including beef cows, dairy cows, veal cows, etc.), processing the supramammary lymph node tissue to degrade the tissue and lyse cells of the tissue, and extracting one or more targeted biological factors from the processed tissue. Following extraction, the one or more biological factors can be purified. In one embodiment the extracted one or more biological factors can be utilized in a culture medium.

The tissue can be processed according to any suitable method. For example, the tissue can be frozen and then homogenized to degrade the tissue.

Similarly, the extraction process can utilize any suitable method including, without limitation, chromatography, solvent extraction, precipitation, centrifugation, and any combination thereof.

The one or more targeted biological factors can be, for example, proteins or lipids, growth factors, and the like. For example, the one or more targeted biological factors can include one or more of interleukin-1, interleukin-2, interleukin-4, interleukin-5, interleukin-6, interleukin-7, interleukin-10, interleukin-12, interleukin-15, granulocyte-colony stimulating factor, macrophage-colony stimulating factor, granulocyte/macrophage-colony stimulating factor, interferon-gamma, immunoglobulins, complement proteins, or enzymes.

BRIEF DESCRIPTION OF THE FIGURES

A full and enabling disclosure, including the best mode, to one of ordinary skill in the art, is set forth more particularly in the remainder of the specification, including reference to the accompanying figures, in which.

DETAILED DESCRIPTION

Figure 1:
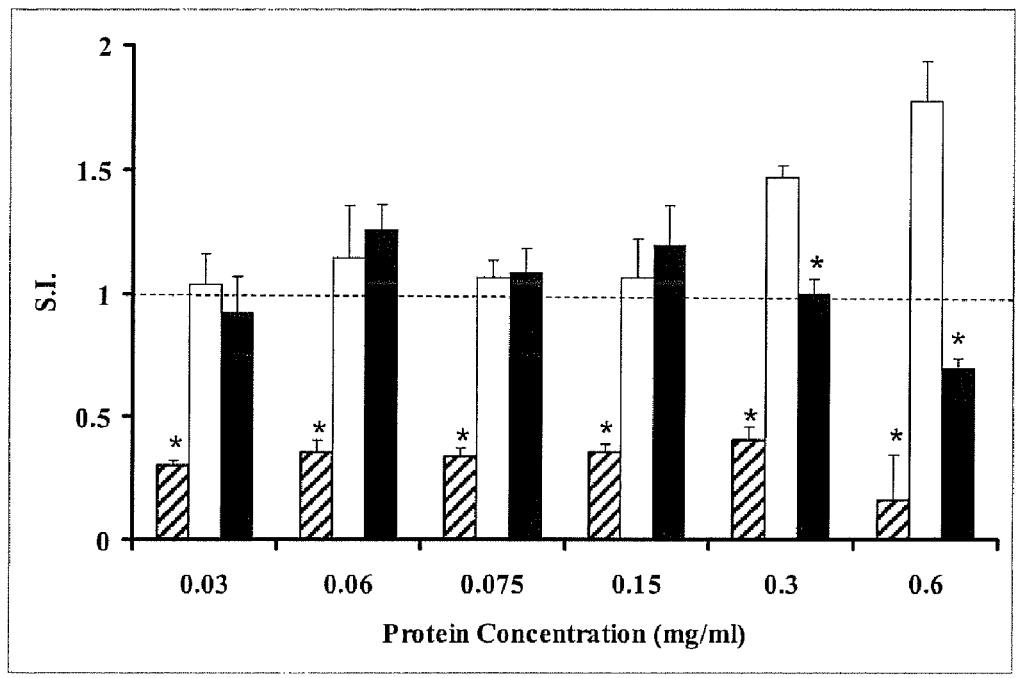
FIG. 1 illustrates the stimulation index (SI) obtained for a human breast cancer epithelial cell line (MDA-MB-435) cultured on either heat-inactivated lymph node extract (LN) (white), non-heat inactivated LN (striped), and bovine growth serum (BGS) (black) following a serum starvation assay.

Reference now will be made to embodiments of the disclosed subject matter, one or more examples of which are set forth below. Each example is provided by way of an explanation of the subject matter, not as a limitation thereof. In fact, it will be apparent to those skilled in the art that various modifications and variations can be made in the disclosed embodiments without departing from the scope or spirit of the subject matter. For instance, features illustrated or described as one embodiment can be used on another embodiment to yield still a further embodiment. Thus, it is intended that the present disclosure cover such modifications and variations as come within the scope of the appended claims and their equivalents.

Definitions

The terms "cell culture" and "tissue culture" as utilized herein generally refer to the process of growth and/or development of cells or tissue in a controlled environment (e.g., in vitro). The term can also refer to the controlled environment itself, usually including the cells or tissue to be cultured.

The term "tissue culture" as utilized herein can generally refer to a culture either of a single tissue or a combination of tissues (e.g., two or more different tissues cultured while in biochemical communication with one another, including an organ).

The terms "medium," "media," "culture medium," and "culturing medium," as used herein and with regard to the disclosed subject matter generally refer to at least a portion of the controlled environment(s) in which cells or tissues are held during culturing. For instance, the term "cell culture medium" can refer to the total environment in which culturing can take place, i.e., including temperature, pressure, materials, etc., as well as to specific components of the environment, e.g., a fluid that can provide nutrients, growth factors, and the like to the developing cells of the culture.

The terms "supplement," "culture supplement," and "culturing supplement," as used herein generally refer to a portion of the controlled environment in which cells or tissues are held during culturing. For instance, a supplement can be a material, e.g., a fluid that can include one or more compounds for delivery to the cells of the culture. For example, a cell culture supplement can provide nutrients, growth factors, enzymes, or other agents to the cell or tissue culture being developed. A supplement can also provide materials useful for controlling the environment of the culture. For example, a supplement can provide pH control, viscosity control, etc., to the culture.

The term "homogenize" as used herein can generally refer to the act of degrading a substance to form smaller particles and dispersing the particles throughout a fluid. The size of the particles formed can depend upon the nature of the starting material as well as on the conditions of the homogenization process. For instance, the particles formed upon homogenization of a tissue can encompass whole cells, lysed cells (i.e., separated cellular components), extra cellular matrix components, portions of membranes, structural components of the tissue, individual proteins, and the like.

The term "biological factor" as used herein generally refers to a naturally occurring molecular compound that can exhibit biological activity.

The term "growth factor" as used herein generally refers to a biological factor capable of stimulating cellular proliferation and/or cellular differentiation.

DESCRIPTION

In one embodiment the present disclosure is directed to methods of forming a proteinaceous product as may be beneficially utilized in a variety of in vitro and in vivo applications. For instance, disclosed products can be utilized in vitro culturing protocol as well as in vivo therapeutic protocols. In particular, though the following discussion is directed primarily to formation and utilization of culturing supplements, it should be understood that the proteinaceous products disclosed herein are not limited to this particular application, and in other embodiments, proteinaceous products as may be formed according to the present disclosure can be utilized in other applications, including, without limitation, other research applications, therapeutic applications, animal husbandry applications, and the like. For instance, disclosed proteinaceous products can be utilized in formation of secondary products, e.g., nutraceuticals, pharmaceuticals, dietary supplements, veterinary products, animal feed, and so on.

In one embodiment, the disclosed compositions can be useful as an additive for use with previously known cell culture supplements or optionally as a replacement for other supplements in cell culture media. For example, the disclosed materials can be utilized as a replacement for FBS in a cell or tissue culturing protocol.

Proteinaceous products as disclosed herein can be formed from a starting material that encompasses specific internal tissue of an animal. Accordingly, in one embodiment, the present disclosure is directed to methods for reducing waste from an abattoir or other animal processing plant. For example, tissue and organs that have in the past been discarded or utilized for little economic benefit to the producer can be collected in order to supply the starting materials for products as described herein. This use of the previously discarded or less profitable tissue can potentially provide a higher income source to the processor.

In another embodiment, the present disclosure is directed toward a method of producing isolated proteins as well as other useful biological factors from a collected tissue. For example, in one embodiment, targeted proteins can be extracted and purified from tissue that in the past was discarded or utilized in a less specific and/or less profitably manner.

The starting materials for formation and development of the disclosed products can be collected during the processing of an animal, for instance during processing performed in an abattoir, meat processing plant, or the like. Animals encompassed by the present disclosure can include any livestock animal. For instance, bovine, ovine, equine, swine, camelidae, and the like. In one embodiment, the process can be directed to larger livestock, as tissue recovery can be carried out more quickly and easily as compared to smaller animals, but this is not a requirement of the present disclosure. In one preferred embodiment, disclosed processes can be directed to bovine.

Tissue utilized as starting materials can be derived from animals of any age. For instance, tissue can be obtained from older animals, such as dairy cows following high production years, or from young animals, such as immature animals under about one year of age or from veal cows.

In general, starting tissue material can be obtained from an animal during post-euthanasia processing. During processing, internal tissue and organs are typically stripped and separated from the carcass, leaving edible meat and other more useful and valuable parts of the carcass. Much of the internal tissue of processed animals is currently deemed by-products and either discarded as waste or processed into relatively low value products, such as pet food, fertilizer, or some other use that provides little economic benefit to the processor and as such, lowers the economic value to the animal producer as well.

Starting materials useful for developing the disclosed products can be collected during the processing of an animal carcass. For example, particular internal tissue such as relatively large and easily separable tissue or organs can be isolated from other tissue of the animal during the normal course of carcass processing. Beneficially, isolating and separating the particular tissue can be carried out within the normal course of carcass processing with little or no additional time or trouble added to the standard process, as the targeted tissue can be easily separable from the remainder of the carcass. In certain embodiments, the particular internal tissue and organs utilized can encompass materials that have been separated from other tissue in the past, but have previously been considered merely waste. As such, the collection of the particular internal tissue as described herein can include merely the collection of what has in the past been considered waste, with no additional carcass processing steps necessary to obtain the desired tissue.

The internal tissue of an animal can provide the starting materials for forming disclosed products. For example, internal tissue can provide proteins as well as other factors, e.g. lipids, fatty acids, etc., which can be utilized in one embodiment in a cell culture medium. More specifically, internal tissue and organs containing useful biological active materials can be collected and processed to form a product that can supply useful biological materials in a beneficial manner. The process can utilize either a single specific tissue type or a combination of different internal tissues and organs, generally depending upon the application desired for the product supplement. For instance, in those embodiments in which only a limited number of specific biological agents are desired in the product, only one or two tissue types can be collected. In another embodiment, several tissue types of the carcass can be combined and processed together to provide a product having a greater variety of useful factors.

In general, targeted tissue for use as starting materials can include tissue of the lymphatic system. For instance, lymph nodes, spleen, thymus, tonsils, and the like can be utilized as starting materials. For example, tissue of the lymph nodes of a bovine can be used in the preparation of a cell culture supplement. The lymph nodes are found along the draining lymphatic system. Generally, nodes are imbedded in tissues with some prominent nodes (e.g., pre-femoral and ischial) located at the bifurcation of draining lymphatic vessels. Due to the nature of the nodes, they can contain a high percentage of constituents, e.g., specialized immune cells that respond to pathogens and antigens in a series of reactions that lead to specific humoral and cell-mediated (i.e., B- and T-cell, respectively) responses so as to impart immunity or protection to the host animal. Specific to these responses are the elaboration of soluble factors (i.e., proteins) that assist in cell proliferation, differentiation and regulation. Thus, in one embodiment, lymph nodes in general or specific lymph nodes can be collected and utilized as starting material for development of culture supplement including a high percentage of one or more of the specialized components of the nodes.

In one embodiment, the supramammary lymph nodes of a female animal can be targeted for utilization as starting material. In one particular embodiment, the supramammary lymph nodes of a bovine, e.g., a dairy or beef cow can be collected for use in the preparation of, e.g., a culture supplement.

The bovine udder or mammary gland is located in the posterior, ventral aspect of the body and is generally the first major organ removed during processing. As the udder is removed from the body, the paired supramammary lymph nodes are exposed at the posterior, dorsal aspect of the udder. The paired nodes are generally visible or at least slightly visible at this point. The nodes may be covered with a thin layer of adipose tissue, but even in this case, the nodes will be somewhat visible. Thus, both nodes can be easily removed from the remainder of the carcass by merely cutting them free of the adhering adipose tissue. Due at least in part to size and relative ease of recovery and isolation during standard animal processing methods, the supramammary glands can be preferred as starting materials in one embodiment of the disclosed processes.

Moreover, the supramammary glands can also be preferred in some embodiments due to the high activity levels of these nodes and the high proportion of specialized biological components they can contain as a result. More specifically, the location of the nodes in the udder is ideal for the function of collecting draining lymph fluids moving from the tissues of the udder toward the more central draining vessels of the lymphatic system, which ultimately empties into the general circulatory system via the lymphatic duct near the heart. The specific purpose of the nodes is to collect and filter any pathogens and antigens that have been introduced into the mammary tissue by infection, milking or purposeful introduction (i.e., vaccination). Thus, the nodes are both large and active and can include large amounts of many components useful for culturing purposes.

For instance, the supramammary lymph nodes and the products that can be formed therefrom can have larger amounts of proteins as well as a wider variety of proteins, than can be found in typical serum, including fetal bovine serum. Supramammary lymph node tissue can include a variety of protein and other cellular factors that can support the growth and development of cellular materials, including, but not limited to, e.g., immunoglobulins such as IgM and IgG; cytokines such as Interleukin-1, Interleukin-2, Interleukin-4, Interleukin-5, Interleukin-6, Interleukin-10, Interleukin-12, Interleukin-15, Interferon-gamma, Tumor necrosis factor-alpha, Macrophage-colony stimulating factor, Granulocyte-colony stimulating factor, and Granulocyte/Macrophage-colony stimulating factor; chemokines such as Interleukin-8 and macrophage inflammatory protein; and any combination thereof.

In one embodiment, tissue target for collection during carcass processing can include the thymus gland. The thymus gland is a central lymphoid organ that is responsible for the generation and differentiation of thymocytes into effector T-cells. The thymus is located in the ventral aspect of the neck between the thyroid glands and the heart. The thymus gland has been targeted for recovery in the past and used as a source material for specific protein products. However, many proteins of the thymus have been overlooked as suitable for recovery and use. In addition, products incorporating the complete protein profile of the thymus have not previously been developed.

The effector T-cells emerging from the thymus "seed" peripheral lymphoid organs (e.g., lymph nodes) are generally considered to be of two classes. There are T-helper cells (TH1 and TH2, both of which are CD4+) and T-cytotoxic cells (CD8+). T-helper cells assist with humoral immunity (i.e., antibody production), while T-cytotoxic cells assist with cell-mediated immunity (i.e., cell killing). Thymus tissue can include a variety of proteins and other growth factors useful for use as a culture supplement including, but not limited to, interleukin-1, interleukin-2, thymopoietin, thymosin, and thymic humoral factor.

In one particular embodiment, the thymus gland of a calf can be collected. Without wishing to be bound by theory, it is believed that the thymus glands of calves, as opposed to more mature cattle, contain more active proteins and less fat due to the age of the calves. The disclosure is not limited to this embodiment, however, and in other embodiments, thymus tissue from older cows, as well as other types of animals, can be targeted for collection.

Following collection, the internal tissue can be preprocessed to improve storage, handling, etc., of the tissue, prior to preparation of a proteinaceous product as may be utilized in any of a number of applications. For instance, following collection, internal tissue may be frozen. Freezing a tissue prior to further processing can improve handling as well as improve preservation of components of the tissue. For instance, freezing a tissue can preserve bioactivity of useful factors such as useful proteins that can then be obtained in a useful format following further processing. Accordingly, freezing a starting material during a preprocessing protocol can lead to a product culture supplement that can contain higher quantities of active proteins.

Freezing collected tissue can generally be carried out according to any suitable method. For example, the tissue can be quickly frozen through immersion in a suitable solvent, such as ethanol, optionally in conjunction with dry ice (i.e., frozen carbon dioxide).

Following any preprocessing, e.g., sorting, freezing, transportation, cleaning, etc., the tissue can be processed to provide one or more components that may be utilized as, e.g., a cell culture supplement. In general, processing of the collected tissue can include the degradation or breaking down of the structure of the tissue, so as to free components of the tissue from one another and from the organized tissue structure. For example, collected tissue can be homogenized during processing.

Homogenization can be performed in the locale where the initial tissue collection occurs, or can be performed in an offsite location and/or following any preprocessing steps, as desired. For instance, in one embodiment a homogenization step can be performed soon after the starting material tissue is isolated and collected, for instance at the abattoir itself. In another embodiment, the tissue can be homogenized following preprocessing. For instance, in one preferred embodiment, the tissue can be homogenized while frozen.

Many methods of tissue degradation are well known in the art, and as such are not discussed at length herein. For instance, any process or method as is generally known in the art can be utilized to homogenize tissue according to the present disclosure. For instance, homogenization can be performed using blenders, pestle and mortar, or the like.

A repetitive freeze/thaw of tissues in combination with a mechanical process such as homogenization can be utilized to degrade the tissue structure. In one embodiment, enzymes can be utilized to enzymatically degrade the tissue. For example, collagenase, elastase, and the like can be utilized either alone or in combination with a mechanical degradation procedure. In general, enzymes that could harm proteins desired for inclusion in a product, e.g., certain proteases, will not be utilized while processing the tissue. Combinations of degradation methods can also be used. For instance multiple homogenization methods can be used. In one embodiment, frozen tissue can be homogenized through use of a blender followed by crushing, such as with a mortar and pestle device.

The level of structural degradation obtained during processing can depend upon the final application of the proteinaceous product. For instance, in one embodiment, the collected tissue can be only slightly broken down, so as to free cells, membranes, and so on, from the tissue structure, while leaving individual cells, structural components (e.g., fibrous component, etc.), and the like, intact.

In another embodiment, a more thorough degradation of the tissue structure can be obtained during tissue processing. For instance, processing can include the complete degradation of the cells and structural components of the tissue, and can include cell lysing and release of organelles and cytoplasm, leaving the molecular components, e.g., proteins, free in the resulting mixture.

Following tissue degradation, a culture supplement can be prepared from the resulting mixture. In one embodiment, the mixture can be utilized as formed, and preparation of the supplement can involve merely apportioning the resulting mixture into desired aliquots. In other embodiments, however, preparation of a culture supplement from the degraded tissue mixture can include additional steps.

For example, the resulting mixture formed upon degradation of the starting material tissue can be combined with a liquid carrier. A liquid carrier can optionally function as a solvent for some or all of the molecular components of the mixture. Organic or aqueous carriers can be utilized, with preference generally depending upon the product application.

In one embodiment, the liquid carrier can be buffered saline. A liquid carrier can provide an active function, e.g., pH control, solvation, etc., or can serve to merely provide desired physical characteristics, e.g., dilution, to the mixture.

In one embodiment, a mixture including the tissue degradation products can be further treated to remove macroscopic materials from the mixture. For example, solids can be removed from the mixture via centrifugation or filtering, leaving the desirable protein constituents as well as other molecular factors in solution.

Without wishing to be bound by theory, it is believed that the variety of biological agents obtainable in culture supplement materials as described herein can improve the growth and/or development of a cell, tissue, or organ culture. For instance, in one embodiment, disclosed culture supplements can provide the complete protein profile of the collected tissue to a culturing protocol. Moreover, disclosed products not only can provide a wide range of desirable materials to a culture medium, e.g., growth factors, enzymes, etc., but can also provide desirable materials in a more consistent fashion from batch to batch as has been previously achieved with serum alone. In addition, disclosed culture supplements can be provided in a less expensive manner than previously known cell culture supplements, such as fetal bovine serum.

A cell culture supplement as described herein can be utilized alone or in combination with other culture supplements. For example, in one embodiment, a culture supplement as described herein can be combined with serum, such as FBS, bovine growth serum, bovine sera, bovine serum albumin, hybridoma growth medium, and the like, to produce a composite cell culture supplement.

Products of the present disclosure are not limited to culture supplements. Moreover, products are not limited to compositions including the complete protein profile of the tissues obtained during a collection protocol. For example, in one embodiment, a mixture including degraded tissue as described above can be further processed to remove one or more proteins or other molecular factors from the mixture. For instance, the mixture can be processed via a separation protocol and one or more specific proteins or other factors can be extracted from the mixture. For instance, one or more unwanted factors can be removed from the mixture, leaving a culture supplement product having a wide variety of useful molecular components.

Specific proteins and/or other useful factors can be extracted from the degraded tissue composition and used either separately or together to provide a beneficial product. For instance, biological factors such as, growth factors, complement proteins, and the like as may be separated from degraded tissue, e.g., lymph node tissue, and used in numerous applications. In particular, it should be understood that products obtained according to the disclosed methods are not limited in use to culture supplements. For instance, one or more isolated factors as described herein can be used in research applications, in pharmaceuticals, as a veterinary food additive, and the like, in addition to being utilized as culture supplement materials.

Specific proteins and/or other molecular factors can be extracted from the processed tissue through any number of methods, including, but not limited to, solvent extractions, chromatography, precipitation, and the like. Multiple extractions or combination of extractions may be utilized to isolate one or more targeted substances from the processed tissue. Additionally, once extracted, the extracted factor can be further purified, to provide a 'pure' (e.g., about 99% purity) factor. Any method of purification can be utilized in accordance with the present disclosure.

According to this embodiment, specific proteins (e.g., enzymes, co-enzymes, cytokines, etc.), lipids (e.g., steroids, prostaglandins, etc.), fatty acids, etc. can be recovered and provided through a more economically friendly process than can be achieved from other processes. For example, purified preparations of specific immunoglobulins, hormones, cytokines, chemokines, complement proteins, enzymes or combinations thereof can be provided in an economical fashion.

Following preparation, products as disclosed herein can be frozen, either prior to or following any other processing steps, for instance to better preserve the useful factors for later use. Freezing the material can provide other benefits as well, for example, the frozen material can be more easily transported to laboratories, distributors, or other users. Prior to use, the frozen mixture can be thawed prior to use.

Reference now will be made to various embodiments of the invention, one or more examples which are set forth below. The examples are provided by way of explanation of the invention, not as a limitation of the invention.

Example 1

Three different established cell lines were examined. A human breast cancer epithelial cell line (MDA-MB-435) was obtained from Tissue Culture Shared Resource at Georgetown University, Lombardi Cancer Center. Hybridoma cells (1C6) were created by fusion of spleen cells of immunized Balb/c mice with SP2/0 myeloma cells. Bovine mammary epithelial cells (MAC-T) were also used.

Supramammary lymph nodes, collected at random, of both beef and dairy cows were obtained from the Brown Packing facility in Gaffney, S.C. The isolated lymph nodes were prepared according to one of two methods, as follows:

Lymph Node Preparation #1:

Initially lymph nodes were trimmed of fat with scissors and homogenized in a food-grade blender with 10 ml of PBS for every five lymph nodes. The extract was then centrifuged for 30 min at 26,500×g. The supernatant was recovered and centrifuged again for 30 min at 32,500×g. Twenty ml of PBS were added to every 10 ml of extract and filter sterilized with serum acrodisc (0.2 µm) syringe filter. The extract was then heat inactivated at 60° C. for 60 min. Non-heat inactivated lymph node extract was prepared the same save for the final step. This lymph node preparation yielded a protein concentration of 3.0 mg/ml. Protein concentration of the lymph node homogenate was determined using the Warburg-Christian protein assay.

Lymph Node Preparation #2:

Lymph nodes were trimmed of fat with scissors and processed through a Hobart meat grinder until moderately homogenous. The homogenate was placed in freezer bags at −80° C. for two days. The frozen lymph node homogenate was then crushed into small pieces under liquid nitrogen in a mortar with pestle and lyophilized for approximately seven days in a Virtis freeze dryer (SP Industries Inc, Warminster, Pa.). The homogenate was then ground into a fine powder using a small food processor. Five grams of the powder was weighed and mixed with PBS in a centrifuge tube to reach a total weight of 50 grams. The solution incubated at room temperature for 20 min and was then centrifuged for 15 min at 739×g. The supernatant was removed and heat inactivated at 60° C. for 60 min. The solution was then centrifuged for 30 min at 7,000×g and filter-sterilized (0.2 µm) with a Nalgene bottle top filter into a sterile container. This preparation yielded a protein concentration of 27.0 mg/ml.

MDA-MB-435 cells were thawed and initially cultured in Dulbecco's Modified Eagles Medium (DMEM) containing 10% bovine growth serum, 1% penicillin/streptomycin, 1% amino acids, 11 mg sodium pyruvate, and 4.0 mM L-glutamine.

The MAC-T cells were cultured in DMEM containing 10% bovine growth serum, 1% penicillin/streptomycin, and 4.0 mM L-glutamine.

The 1C6 cells were cultured with DMEM containing 10% bovine calf serum, 1% penicillin/streptomycin, 11 mg sodium pyruvate, 238 mg HEPES, 100 ml 2-mercaptoethanol, and 4.0 mM L-glutamine. All cells were cultured in 75 $cm^2$ flasks and incubated at 37° C. in a humidified, water-jacketed CO2 (5%) incubator.

MTT Assay with MDA-MB-435 cells

The MTT [(3-(4, 5-Dimethylthiazol-2-yl)-2, 5-diphenyltetrazolium bromide), Sigma-Aldrich, St. Louis, Mo.] cell viability assay was used to assess the cellular activity of MDA-MB-435 breast cancer epithelial cells exposed to lymph node extract supplementation in culture medium.

Cells were trypsinized with HyQ® Trypsin (0.25%) and centrifuged for 5 min at 400×g. The supernatant was removed and the cells were re-suspended in approximately 2 ml of medium. Cells were counted and added to a 96-well plate with 10,000 cells/well and held overnight in a CO2 incubator to adhere. One day later, all media was removed and the wells were rinsed two times with 100 µl sterile PBS. The appropriate media were then added to the wells without serum and incubated for a 2 day starvation period.

Lymph node and bovine growth serum (BGS) media were made at different percentages with DMEM. 0, 1, 2, 2.5, 5, 10 and 20% media were added to the plates at 100 µl/well. Zero percent medium was made without serum or lymph node extract as control. Heat inactivated and non-heat inactivated lymph node preparation #1 was used for the MTT assay. In order to maintain an equal protein concentration across treatments, BGS and non-heat inactivated lymph node extract were diluted with PBS to the concentration of the heat inactivated lymph node extract (3.0 mg/ml). For the 1% media, 1 ml of 3.0 mg/ml BGS and lymph node extract (0.03 mg/ml) was added to 99 ml of MD-MBA-435 media with the appropriate components. For 2%: 2 ml was added to 98 ml (0.06 mg/ml), 2.5%: 2.5 ml was added to 97.5 ml (0.075 mg/ml), 5%: 5 ml was added to 95 ml (0.15 mg/ml), 10%: 10 ml was added to 90 ml (0.3 mg/ml), and for 20%: 20 ml was added to 80 ml (0.6 mg/ml).

At day 4, 50 µl of MTT was added to each well four hours prior to end of incubation. The media including MTT was then removed and 150 µl of DMSO was added to each well. The plate was placed on a shaker for approximately 15 minutes. Absorbance was obtained at wavelengths 570 and 650 nm for each well. The O.D. by difference was recorded for each well.

Results are illustrated in FIG. 1 and are expressed as stimulation indices (S.I.=O.D. supplemented media/O.D. 0% supplemented media) of cell viability assessed through MTT reduction. Specifically, FIG. 1 illustrates results with the various supplements including heat-inactivated lymph node extract (LN) (white), non-heat inactivated LN (striped), and BGS (black). Bars marked with an asterisk are results in which the S.I. was found to be significantly different ($P \leq 0.05$) from respective mean for the heat inactivated LN. A stimulation index above 1 is representative of cell viability greater than the control group (0% serum or lymph node extract).

As can be seen in FIG. 1, heat inactivated lymph node extract supported significantly greater cell viability at 10 and 20% supplementation (0.3 and 0.6 mg/ml protein) than observed for both BGS and non-heat inactivated lymph node extract ($p<0.0001$). As low as 1% (0.03 mg/ml) heat inactivated lymph node extract was found to support cell viability better than the traditional BGS supplementation at the same percentage. 1% heat inactivated lymph node extract also supported viability better than 10% and 20% BGS. BGS did support cell viability at 2, 2.5 and 5% supplementation, with marginal support at 10%.

Non-heat inactivated lymph node extract did not sustain cell viability at any concentration. This is believed to be due to complement proteins in the extract that can be inactivated with heat, which was done with a matched extract. BGS and other bovine sera used in cell culture are routinely heat inactivated to remove complement, which is a heat sensitive factor.

CyQuant Assay

The CyQuant assay was used to determine the degree of DNA synthesis and cellular proliferation through direct DNA staining with the CyQuant GR fluorescent dye. CyQuant GR dye and 20× cell lysis buffer were purchased from Invitrogen (Carlsbad, Calif.). Serum starvation assay was run according to the protocol of MTT assay until addition of CyQuant GR dye. Lymph node preparations #1 and #2 were used in the CyQuant assay. MDA-MB-435 cells were treated with both preparations in two separate CyQuant assays, and MAC-T and 1C6 cells were treated with only lymph node preparation #2. (Lymph node preparation #2 yielded the following protein concentrations: 1%: 0.27 mg/ml, 2%: 0.54 mg/ml, 5%: 1.35 mg/ml, 10%: 2.7 mg/ml, 20%: 5.4 mg/ml.)

After 3 days with the different treatments the plates were inverted and blotted. The CyQuant GR dye/lysis buffer contained 1.2 ml of 20× lysis buffer, 22.8 ml nuclease free distilled water, and 60 µl of CyQuant GR dye. Two hundred µl of dye/lysis buffer were added to all wells. Plates were mixed gently and incubated for 2 to 5 min with covers to protect from light. Plates were read on a BioTek Synergy HT plate reader at excitation of 480 and emission of 520 nm. Fluorescence intensity of each well was recorded.

The results are illustrated in FIGS. 2-5 including results for heat-inactivated LN (white), non-heat inactivated LN (striped), and BGS (black). Results are expressed as a proliferation index (P.I.=fluorescence intensity of supplemented media/fluorescence intensity of 0% supplemented media). A proliferation index above 1 (indicated by the dashed line in FIGS. 2-6) is indicative of cell proliferation greater than the control group (0% serum or lymph node extract). Those bars marked with an asterisk have a P.I. significantly different ($P \leq 0.05$) from the respective mean obtained for heat inactivated LN materials.

Figure 2:
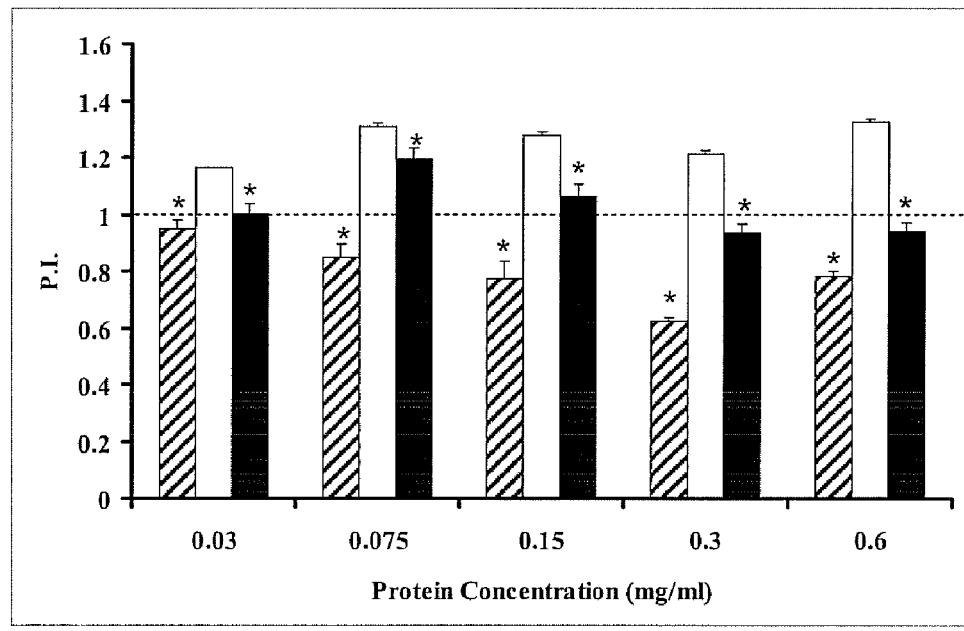
FIG. 2 illustrates the proliferation index obtained for MDA-MB-435 cells cultured on heat-inactivated LN (white), non-heat inactivated LN (striped), and BGS (black)

FIG. 2 illustrates proliferation results of MDA-MB-435 cells with lymph node preparation #1 (3.0 mg/ml). As can be seen, the heat inactivated extract supported proliferation better than both non-heat inactivated lymph node extract and BGS at all percentages of supplementation. BGS best supported cell proliferation at 2.5% (0.075 mg/ml protein), followed by a decline in proliferation from 5 to 20%. One percent heat inactivated lymph node extract supported cell proliferation better than 5, 10, and 20% supplementation with BGS.

In concurrence with FIG. 1, a lower protein concentration of 0.03 mg/ml (1%) heat inactivated lymph node extract was found to support cells better than the standard BGS supplement at the highest three protein concentrations tested. Non-heat inactivated lymph node extract did not support cell proliferation at any percentage as evidenced by the apparent inhibitory level of cell proliferation demonstrated in FIG. 2.

Figure 3:
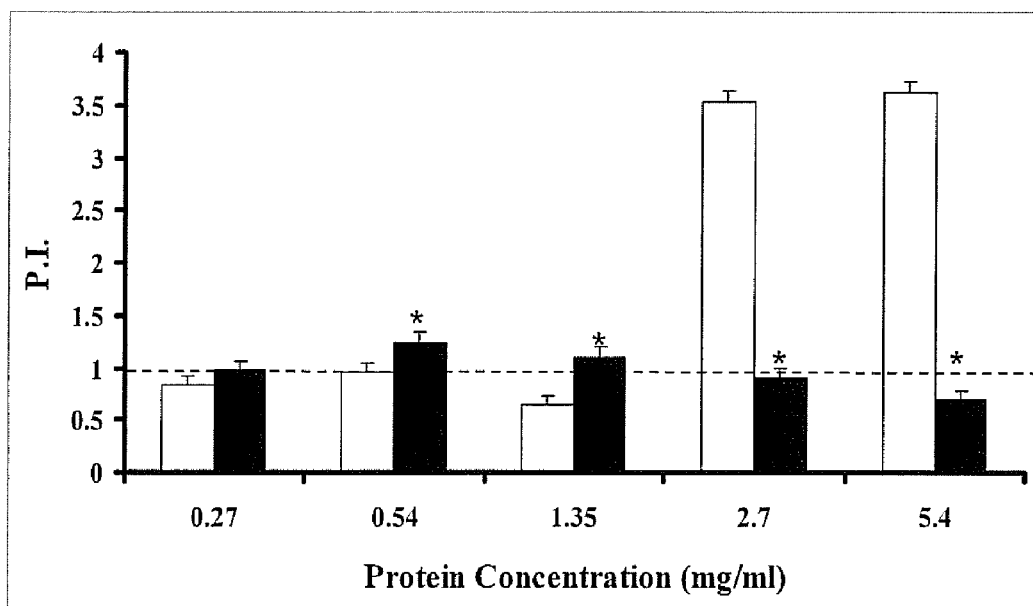
FIG. 3 illustrates the proliferation index of MDA-MB-435 cells cultured on heat-inactivated LN (white) and BGS (black)

MDA-MB-435, MAC-T, and 1C6 cells were also cultured with heat inactivated lymph node preparation #2. FIG. 3 illustrates the effects of lymph node preparation #2 on MDA-MB-435 cells. The proliferation of cells cultured with BGS and heat inactivated lymph node extract is significantly different ($P<0.0001$) at all percentages except 1% supplementation (0.27 mg/ml protein). BGS maintained cell proliferation at or slightly above the 0% control from 1-5%, with a slight drop at 10 and 20% supplementation (2.7 and 5.4 mg/ml protein). The heat inactivated lymph node extract maintained cell proliferation below the 0% control from 1-5% supplementation; however, MDA-MB-435 cells exhibited a dramatic increase in proliferation with heat inactivated lymph node extract at 10 and 20% supplementation. This latter effect of heat inactivated lymph node extract resulted in a significant supplementation by percent supplementation interaction ($P<0.0001$).

Figure 4:
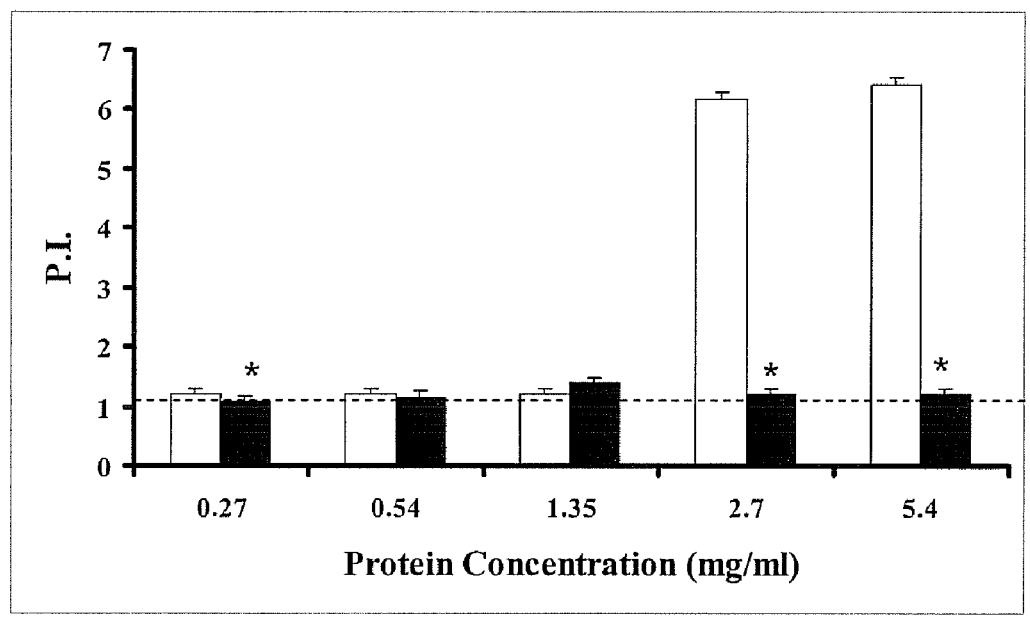
FIG. 4 illustrates the proliferation index of bovine mammary epithelial cells (MAC-T) cells cultured on heat-inactivated LN (white) and BGS (black)

MAC-T cell proliferation was found to be significantly different between BGS and heat inactivated lymph node extract cultured cells at 1, 10, and 20% supplementations (FIG. 4). BGS maintained cell growth at or slightly above the 0% control throughout all percent supplementations. Heat inactivated lymph node extract supported cell proliferation slightly above the 0% control from 1-5% supplementation. Similar to the results with the MDA-MB-435 cells, MAC-T cells showed a dramatic increase in proliferation at 10 and 20% supplementation leading to a significant interaction effect ($P<0.0001$).

Figure 5:
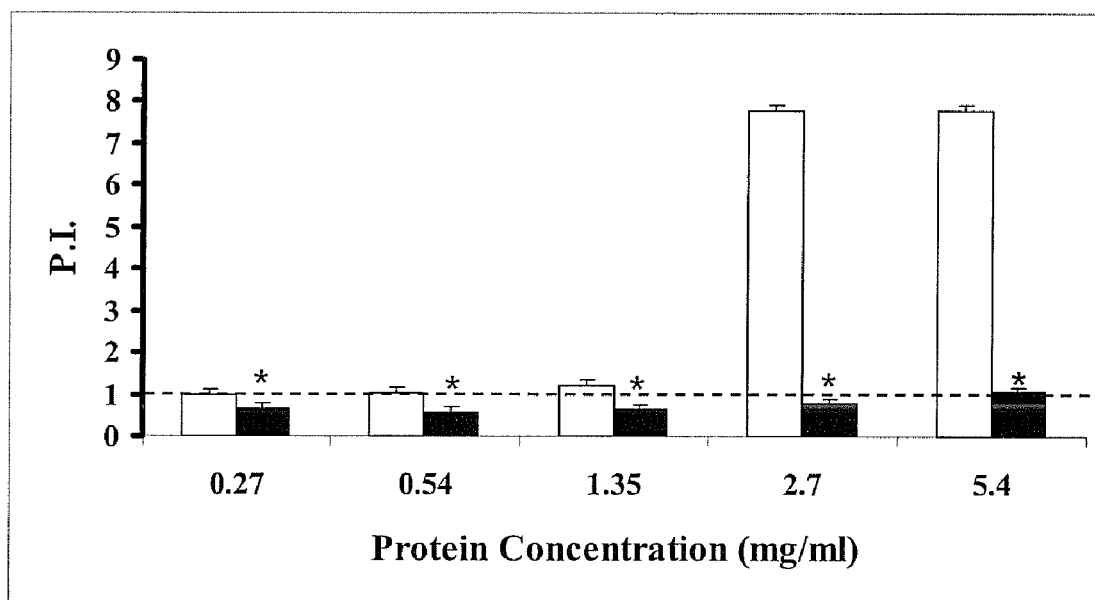
FIG. 5 illustrates the proliferation index of hybridoma cells (1C6) cells cultured on heat-inactivated LN (white) and BGS (black)

1C6 cell proliferation was significantly different between BGS and heat inactivated lymph node extract at all percent supplementations ($P<0.0001$) (FIG. 5). BGS maintained cell proliferation slightly below the 0% control at 1, 2, 5, and 10% supplementations, and right at the 0% control level at 20%. Heat inactivated lymph node extract maintains cell proliferation at or above the 0% control at 1, 2, and 5% supplementations. In agreement with MDA-MB-435 and MAC-T cells, 1C6 cells also showed a dramatic increase in proliferation at 10 and 20% supplementation and a significant interaction for supplementation source and percent supplementation ($P \leq 0.001$).

Cell Growth Assays

To grow cells directly in lymph node media a direct suspension method (adherence growth assay) as well as a modified adaptation method were used. Lymph node extract from lymph node preparation #2 was used for the cell growth assays. Both assays used 10% lymph node medium with 1×DMEM as well as other medium components appropriate for the specific cell line in culture. BGS was diluted with PBS in order to maintain all treatments at an equal protein concentration. A protein concentration of 2.7 mg/ml (10% of 27 mg/ml lymph node extract stock) was maintained throughout the assays. Diluted serum media was used as a positive control as well as a 0% serum/lymph node medium as a negative control.

Adherence Growth Assay

Cells were cultured to 100% confluency in regular media containing 10% serum (BGS or BCS). Cells were then trypsinized and re-suspended in 2 ml of serum/lymph node-free medium. Once cells were counted they were seeded at 10,000 cells/well in 24-well plates with appropriate treatment media. Each treatment covered 12 wells. Five hundred µl of treatment medium was added to each well. Cells adhered overnight and were examined once daily for 6 days using an inverted microscope fitted with a digital camera.

MDA-MB-435 cells as well as MAC-T were cultured in respective treatment media. Media without serum or lymph node extract were used as negative controls (0%). Media with 10% bovine growth serum diluted to an equal protein concentration (2.7 mg/ml) were positive controls (BGS). Media were also made with 10% lymph node extract (LN). The plates were visually assessed to rate cell growth and adhesion. On Day 1, with 0% supplementation, MAC-T cells did not appear to be actively proliferating, but did illustrate minimal adherence and spreading. Day 1 with BGS, MAC-T cells illustrated normal spreading, unlike cells with the LN which did not adhere or spread and did not have a healthy appearance. Days 2 and 3 continued the trend observed on Day 1 with the MAC-T cells and respective treatments. By Day 4 the LN treated cells had crenated membranes and cell debris was present. On Day 4 the MAC-T cells with BGS continued to grow to confluency, and the 0% serum cells were not proliferating or spreading out. Days 5 and 6 illustrated similar results as Day 4, with confluency (BGS), cell debris and apparent death (LN), and a halt in proliferation (0%). The cell membranes of the lymph node treated cells appeared picnotic compared to BGS and 0% supplemented cells at any time point. The MDA-MB-435 cells showed a trend similar to the MAC-T cells with all treatments. On Day 2 MDA-MB-435 cells showed 0% and BGS supplemented cultures had cells beginning to spread out (0% very minimally), with LN cells already presenting shriveled, crenated membranes and un-adhered cells. Day 3 illustrated similar results as Day 2 for LN and 0% cells, with increased confluency of BGS supplemented cells. On days 4 through 6 MDA-MB-435 cells showed proliferation of cells with BGS, rounded clustered cells (halted growth) with 0% supplementation, and cell debris along with apparent cellular death with LN.

Adaptation Growth Assay

Cells were cultured to nearly 100% confluency in standard medium containing non-diluted 10% serum (approximately 6.6 mg/ml of BGS or BCS) in a cm² flask as well as a six well plate. Once confluent, all media were removed and 25% of 2.7 mg/ml lymph node media was added along with 75% regular media with BGS.

For the MDA-MB-435 cells as well as the MAC-T cells trypsin was added on Day 5 and cells were re-seeded into a new flask. 1C6 cells were scraped and re-seeded into a new flask. Cells were incubated overnight to adhere. This was done to evaluate the "adapted" cells ability to re-adhere with only lymph node medium in culture. Cell growth in the flasks and plates was assessed through visual analysis. Detachment of cells resulting in floating cells, cellular debris, and standard attachment and spreading out, were characteristics of cells observed in the cultures.

Day 1 for all cell lines represented confluency without any LN media. Day 2 represents 25% of 10% LN media addition, Day 3: 50% of LN media addition, Day 4: 75% LN media addition, Day 5: 100% of 10% LN medium. Day 6, with the different cell lines in the flasks, represents cells after trypsinization or scraping. MAC-T cells in the plate and flask (up to Day 5) maintained confluency and normal morphology. On Day 6, after trypsinization, the cells did not re-adhere and cell debris was present. The MDA-MB-435 cells followed the same trend as the MAC-T cells with confluency in the plate and flask up to Day 5. Day 6, after trypsinization, did not show any adherence of cells, and the few floating cells appeared dead. Cell debris was not as prevalent as it was with the MAC-T cells. 1C6 cells did not maintain confluency like the MDA-MB-435 and MAC-T cells. Days 1 and 2 cells are confluent, but with 50% lymph node media addition on Day 3, 1C6 cells seem to have a change in morphology as well as a decrease in confluency. The cells were rounding up by Day 3 and all had a picnotic membrane appearance. 1C6 cells continue to change morphology on Days 4 and 5 with a significant decrease in confluency on Day 5 with the full 10% lymph node extract in the medium. When 1C6 cells were scraped and re-seeded, these cells were unable to adhere. Few remained floating and appeared dead.

As the lymph node extract was gradually added to the media with BGS still present in reduced percentages the cells appeared to adapt fairly well. The 1C6 cells did not thrive as well as the MAC-T or MDA-M-435 cells and began to round up at day 3. The morphology of the 1C6 cells changed, with a loss of their round full membranes and a more crenated membrane appearance.

The inability of cells to adhere following re-seeding is believed to be due to the 'stimulation overload' presented by the lymph node extract. Cells, such as human corneal epithelial cells, have been shown to grow without serum present in medium. When considering cells that can maintain growth without serum, the addition of lymph node extract might provide a greater amount of growth promoting factors that would favor excessive mitogenesis rather than maintenance of steady-state growth. Cells exposed to the lymph node extract were being stimulated with more and different protein than the cells are normally accustomed to in BGS. The abundance of proteins in the extract may have offered too many mitogenic signals at one time for the cells to respond with adherence.

Example 2

BGS as well as lymph node preparation #2 described above in Example 1 were run on a sodium dodecyl sulfate polyacrylamide gel electrophoresis (SDS PAGE) 12% Tris/HCl gel. Samples were denatured with SDS PAGE sample buffer (100 mM Tris, 2% SDS, 5% β-mercaptoethanol, and 15% glycerol) and boiled for 5 minutes. Five μl of each sample were loaded on a 30 μg/ml basis with GelCode® Blue Stain Reagent (Pierce Biotechnology, Inc., Rockford, Ill.) along with 2 Biorad Precision Plus Protein Dual Color Standards (Bio-Rad Laboratories, Inc., Hercules, Calif.). The gel was run at 120 volts for 1 h.

Figure 6:
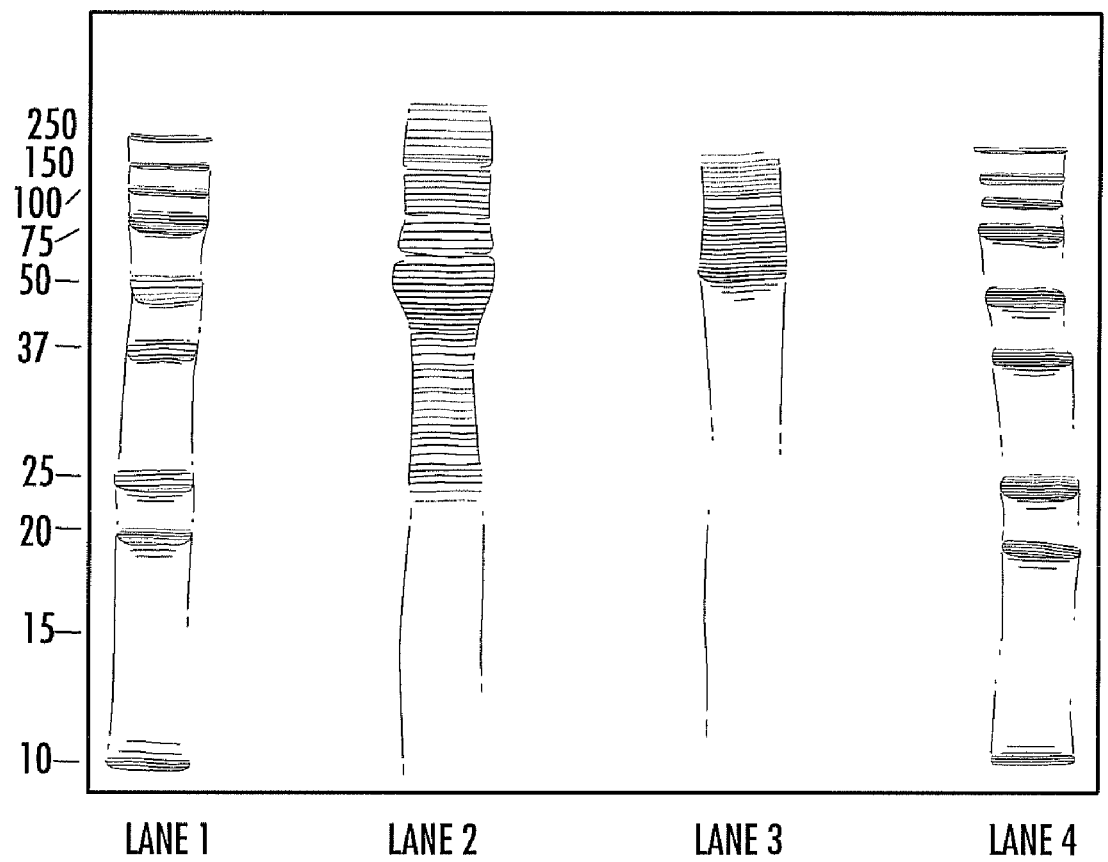
FIG. 6 illustrates an SDS PAGE analysis of BGS and LN.

FIG. 6 illustrates protein bands from both BGS and lymph node preparation #2 extract. Lanes 1 and 4 represent protein standards. BGS (Lane 2) has very heavy staining bands at 50 kDa and above, which is most likely immunoglobulin heavy chains and albumin. Lymph node extract (Lane 3) has a less intense albumin band, as well as an array of bands spanning the length of the standards. There are obvious differences in protein composition between BGS and the lymph node extract based on this protein gel.

Example 3

Supramammary lymph nodes were harvested from cows at slaughter (Brown's Packing, Gaffney, S.C.), and fat and other connective tissues were removed. Nodes were ground with a tabletop meat grinder (Hobart) and frozen at −80° C.

Working Stock Preparation

A working stock lymph node preparation was formed as described above for lymph node preparation #2.

Ammonium Sulfate Fractionation

Ammonium sulfate (AS) solutions were prepared by adding AS powder to 10 ml distilled, deionized water and stirring until AS was dissolved. Ten ml of lymph node working stock was added to the flasks, which were then placed in beakers, covered with ice, and stirred for 30 minutes. The solutions were transferred to thick-walled 15 ml conical tubes and centrifuged at 9000×g for 30 minutes. Each solution was dialyzed against phosphate buffered saline (PBS) using SnakeSkin® Pleated Dialysis Tubing (Pierce, Rockford, Ill.; 7,000 MWCO) until the osmolarity reached 280-320 mOsm/kg. The osmolarity was measured using a vapor pressure osmometer.

Chondrocyte Harvest

Scapular cartilage was harvested from euthanized adult horses (n=3). Muscle and connective tissue were removed and cartilage was washed with 70% ethanol. Cartilage was minced and transported on ice in medium containing DMEM (with 4.5 g/L glucose; without L-glutamine and sodium pyruvate) and 5× antibiotics (penicillin, 200 units/ml; streptomycin, 200 μg/ml; amphotericin, 0.5 μg/ml), followed by overnight digestion with collagenase (1.85 mg/ml), DNAase (50 μg/ml), and hyaluronidase (50 μg/ml) at 37° C. under stirred conditions. Following digestion, the medium was poured through a cell strainer and centrifuged at 1000×g for 20 minutes at 23° C. The cell pellet was resuspended in medium containing DMEM, 10% BGS (HyClone, Logan, Utah), and 2× antibiotics. Cells were placed in a 75 cm$^2$ tissue culture flask and incubated at 37° C. (5% CO2). At confluency, medium was removed, and cells were washed with PBS and tripsinized. The cell suspension was centrifuged for 20 minutes at 1000×g. Cells were counted using a hemacytometer and resuspended to a concentration of 1×10$^6$ cells/ml in medium containing 50% bovine growth serum (BGS) and 5% DMSO. Cells were frozen overnight at −80° C., then stored in liquid nitrogen.

Cell Culture

Chondrocytes were thawed and cultured in DMEM, 10% BGS, and 2× antibiotics as described above. At confluency, cells were washed, trypsinized for 10-15 minutes at 37° C., and passaged into 96 well plates at a density of 5000 cells per well (Day 0). On Day 3, medium was removed, cells were washed with PBS, and treatment medium was added, as described below. Just prior to cell culture, the freeze-dried supplement was resuspended in DMEM with antibiotics to ensure the volume of DMEM also remained the same for every treatment. The control medium for all experiments was DMEM and antibiotics. On Day 7, treatment medium was removed and plates were stored at −20° C. Each experiment was performed with each of the three primary chondrocyte isolates, with multiple replicates for each treatment.

The protein concentration of each supplement was determined according to standard methods. The protein concentration of BGS was found to be 68.0 mg/ml±4.2 (SEM), the protein concentration of LN was found to be 23.6 mg/ml±0.9 (SEM), and the protein concentrations of ammonium sulfate fractions were found to be 2.9 mg/ml±0.2 (SEM) and 2.2 mg/ml±0.3 (SEM), for 20% AS and 30% AS, respectively.

Figure 7:
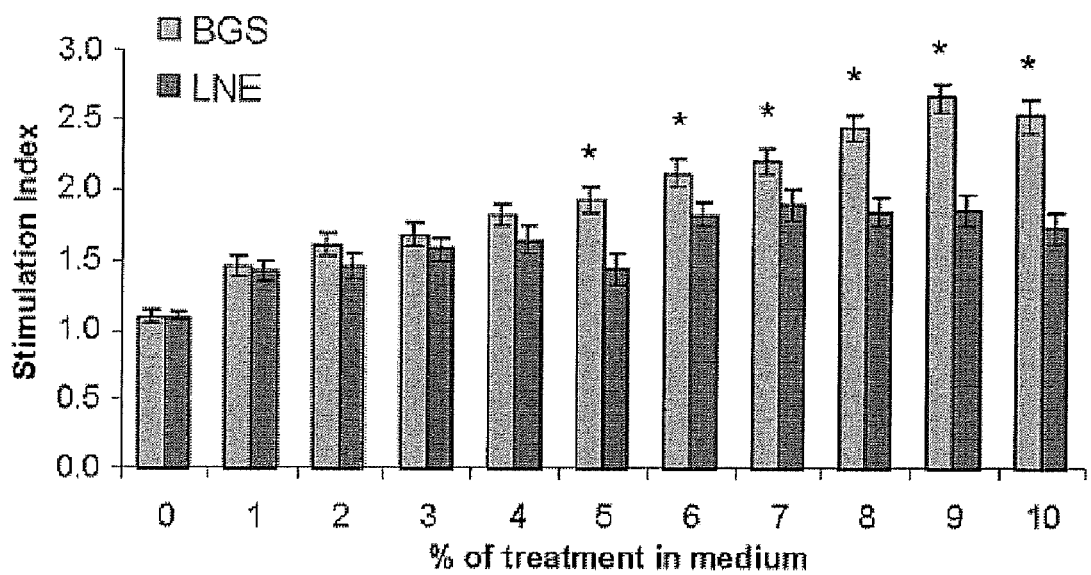
FIG. 7 illustrates cell proliferation results of equine chondrocytes cultured on BGS and LN on an equal volume/unequal protein basis.

Chondrocyte proliferation in response to treatment with media containing 0-10% (v/v) BGS and LN was investigated. Results are shown in FIG. 7. As can be seen, cell proliferation was generally lower for cells cultured in LN. Considering the respective protein values of BGS and LN (68.0 mg/ml±4.2 and 23.6 mg/ml±0.9, respectively), the results are not surprising.

Figure 8:
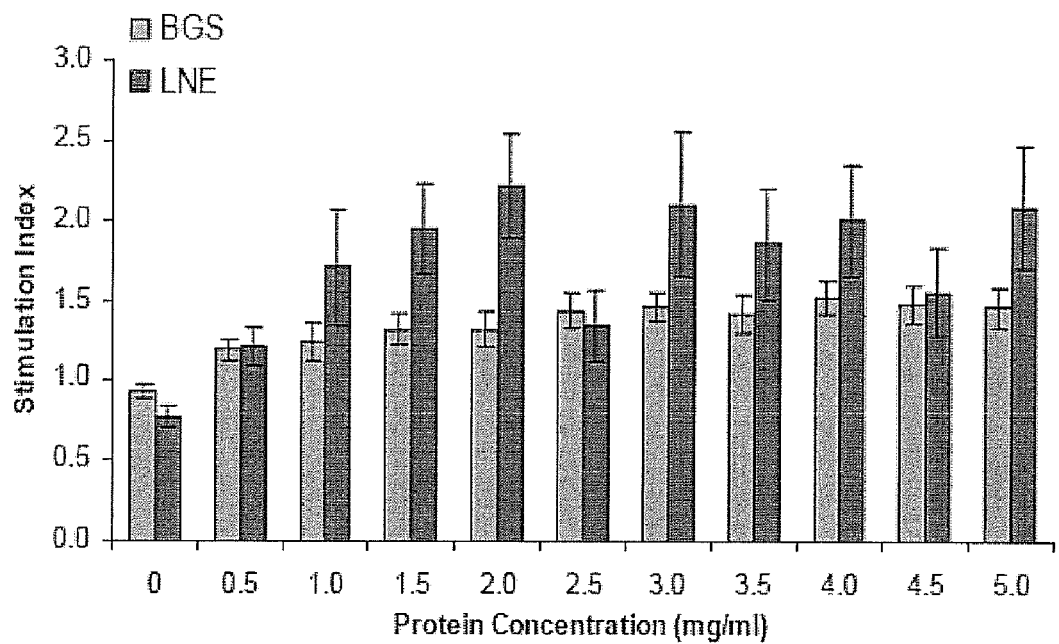
FIG. 8 illustrates cell proliferation results of equine chondrocytes cultured on BGS and LN on an equal protein basis.

Cell proliferation was also compared in response to treatment media containing BGS and LN on an equal protein basis. Results are shown in FIG. 8. As can be seen, chondrocytes cultured in LN responded as well or better as those cultured in BGS.

Figure 9:
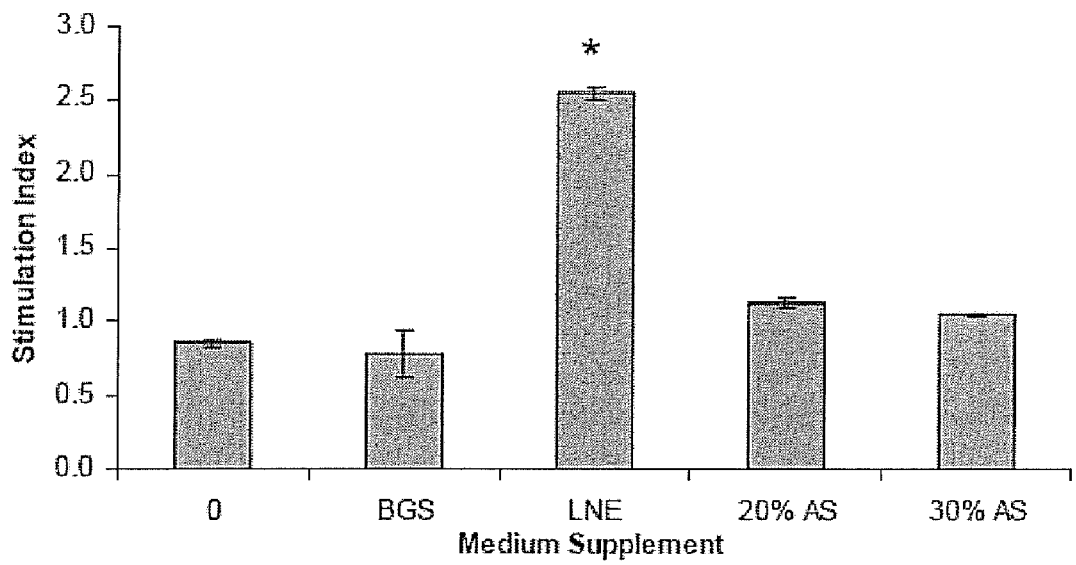
FIG. 9 illustrates cell proliferation results of equine chondrocytes cultured on BGS, LN, and LN fractions precipitated from various concentrations of an ammonium sulfate solution.

Chondrocytes cultured in treatment media containing LN fractions from ammonium sulfate precipitation were compared to cells cultured in media containing BGS and LN. All media contained an equal protein load (1.5 mg/ml). Results are shown in FIG. 9. As can be seen, cells cultured in LN at 1.5 mg/ml exhibited greater proliferation than cells receiving BGS or either AS fraction on an equal protein basis.

Figure 10:
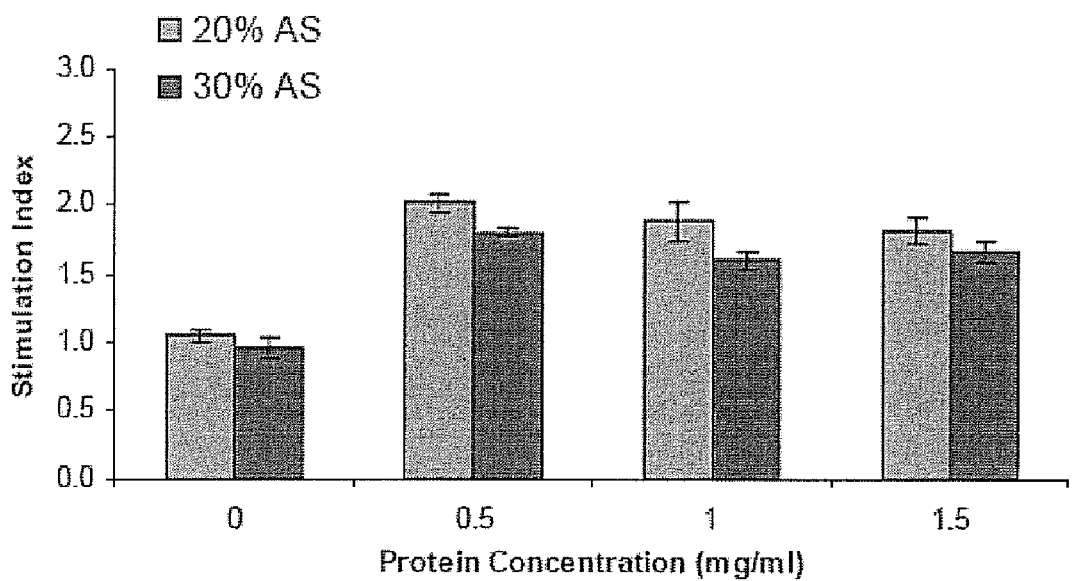
FIG. 10 illustrates proliferation results of equine chondrocytes cultured on a variety of protein concentrations on LN fractions precipitated from various concentrations of an ammonium sulfate solution.

When comparing just the AS fractions over a range of protein concentrations (0.5 mg/ml±1.5 mg/ml), no difference in proliferation was found between the 20% fraction and the 30% fraction at any concentration (FIG. 10). However, cells cultured in media containing the 20% AS fraction at 0.5 mg/ml and 1.0 mg/ml and the 30% AS fraction at 0.5 mg/ml showed a significant increase in proliferation over cells cultured in the control medium.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged either in whole or in part. Furthermore, those of ordinary skill in the art will appreciate that the foregoing description is by way of example only, and is not intended to limit the invention so further described in the appended claims.

The invention claimed is:

1. A method of isolating one or more specific biological factors from supramammary lymph node tissue of an animal, comprising
    collecting supramammary lymph node tissue from an animal carcass;
    processing the supramammary lymph node tissue to degrade the tissue and lyse cells of the tissue; and
    extracting one or more targeted biological factors from the processed tissue.

2. The method according to claim 1, wherein the animal is a bovine.

3. The method according to claim 1, wherein a single biological factor is extracted.

4. The method according to claim 3, the method further comprising purifying the extracted biological factor.

5. The method according to claim 1 further comprising including the one or more extracted biological factors in a culture medium.

6. The method according to claim 1, wherein the step of processing the supramammary lymph node comprises
    freezing the supramammary lymph node; and
    homogenizing the frozen supramammary lymph node.

7. The method according to claim 1, wherein the step of extracting the one or more targeted biological factors comprises chromatography.

8. The method according to claim 1, wherein the step of extracting the one or more targeted biological factors comprises solvent extraction.

9. The method according to claim 1, wherein the one or more targeted biological factor comprises a protein.

10. The method according to claim 1, wherein the one or more targeted biological factor comprises a lipid.

11. The method according to claim 1, where in the one or more targeted biological factor comprises a growth factor.

12. The method according to claim 11, wherein the one or more targeted growth factor is selected from the group consisting of interleukin-1, interleukin-2, interleukin-4, interleukin-5, interleukin-6, interleukin-7, interleukin-10, interleukin-12, interleukin-15, granulocyte-colony stimulating factor, macrophage-colony stimulating factor, granulocyte/macrophage-colony stimulating factor, interferon-gamma, immunoglobulins, complement proteins, enzymes, and combinations thereof.

13. A method of isolating a specific protein from supramammary lymph node tissue of a bovine, comprising
    isolating the supramammary lymph node of a bovine;
    collecting the supramammary lymph node;
    homogenizing the collected supramammary lymph node to produce a homogenized mixture; and
    extracting a targeted protein from the homogenized mixture.

14. The method according to claim 13, wherein the targeted protein is selected from the group consisting of interleukin-1, interleukin-2, interleukin-4, interleukin-5, interleukin-6, interleukin-7, interleukin-10, interleukin-12, interleukin-15, granulocyte-colony stimulating factor, macrophage-colony stimulating factor, granulocyte/macrophage-colony stimulating factor, interferon-gamma, immunoglobulins, complement proteins, enzymes, and combinations thereof.

15. The method according to claim 13, further comprising freezing the supramammary lymph node.

16. The method according to claim 13, wherein the step of extracting the targeted protein comprises chromatography.

17. The method according to claim 13, wherein the step of extracting the targeted protein comprises solvent extraction.

18. The method according to claim 13, wherein the bovine is a dairy cow.

19. A method of isolating a specific proteinaceous growth factor from supramammary lymph node tissue of a dairy cow, comprising
    isolating the supramammary lymph node of a dairy cow;
    collecting the supramammary lymph node from the dairy cow;
    freezing the collected supramammary lymph node;
    homogenizing the frozen supramammary lymph node to produce a homogenized mixture; and
    extracting a proteinaceous growth factor from the homogenized mixture.

20. The method according to claim 19, wherein the proteinaceous growth factor is selected from the group consisting of interleukin-1, interleukin-2, interleukin-4, interleukin-5, interleukin-6, interleukin-7, interleukin-10, interleukin-12, interleukin-15, granulocyte-colony stimulating factor, macrophage-colony stimulating factor, granulocyte/macrophage-colony stimulating factor, interferon-gamma, immunoglobulins, complement proteins, enzymes, and combinations thereof.

21. The method according to claim 19, wherein freezing the supramammary lymph node comprises immersing the collected supramammary lymph node into a mixture comprising dry ice and a liquid solvent.

22. The method according to claim 19, wherein extracting the specific proteinaceous growth factor is achieved by a process selected from the group consisting of chromatography, solvent extraction, precipitation, centrifugation, and any combination thereof.

* * * * *